United States Patent
Seifi

(10) Patent No.: US 10,898,451 B2
(45) Date of Patent: Jan. 26, 2021

(54) METHODS OF TREATING ANTI-NMDA RECEPTOR ENCEPHALITIS WITH TRAMADOL

(71) Applicant: Board of Regents of the University of Texas System, Austin, TX (US)

(72) Inventor: Ali Seifi, San Antonio, TX (US)

(73) Assignee: BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/281,985

(22) Filed: Feb. 21, 2019

(65) Prior Publication Data

US 2019/0262283 A1 Aug. 29, 2019

Related U.S. Application Data

(60) Provisional application No. 62/634,248, filed on Feb. 23, 2018.

(51) Int. Cl.
*A61K 31/135* (2006.01)
*A61P 29/00* (2006.01)
*A61K 9/00* (2006.01)
*A61K 35/16* (2015.01)

(52) U.S. Cl.
CPC .......... *A61K 31/135* (2013.01); *A61K 9/0019* (2013.01); *A61K 35/16* (2013.01); *A61P 29/00* (2018.01)

(58) Field of Classification Search
CPC .... A61K 31/135; A61K 35/16; A61K 9/0019; A61P 29/00
See application file for complete search history.

(56) References Cited

U.S. PATENT DOCUMENTS 8,895,622 B2 * 11/2014 Kottayil ............... A61K 31/485
514/646

OTHER PUBLICATIONS

Honnorat, "Therapeutic approaches in antibody-associated central nervous system pathologies", 2014, Revue Neurologique, 170(10), pp. 587-594. (Year: 2014).*
Dengler et al., "Tramadol may increase the efficacy of therapeutic plasma exchange in anti-NMDAR encephalitis", 2017 (available online May 2017), vol. 160, pp. 38-39. (Year: 2017).*
Pham et al., "Therapeutic Plasma Exchange for the Treatment of Anti-NMDA Receptor Encephalitis", 2011, Journal of Clinical Apheresis, 26(6), pp. 320-325. (Year: 2011).*
Dalmau, J. et al., Paraneoplastic Anti-N-Methyl-D-Asparate Receptor Encephalitis Associated with Ovarian Teratoma. Ann Neurol. 2007; 61(1):25-36.
Grond, S. and Sablotzki, A., Clinical Pharmacology of Tramadol. Clin Pharmacokinet. 2004; 43(13):879-923.
Hara, K. et al., The Effects of Tramadol and Its Metabolite on Glycine, γ-Aminobutyric AcidA, and N-Methyl-D-Asparate Receptors Expressed in Xenopus Oocytes. Anesth Analg. 2005; 100(5):1400-5.
Nosadini, M. et al., Immune Therapy in Autoimmune Encephalitis: a Systematic Review. Expert Rev Neurother. 2015; 15(12):1391-419.
Seifi, A. and Kitchen, D.L., Management of Dyskinesia in Anti-NMDAR Encephalitis with Tramadol. Clin Neurol Neurosurg. 2016; 147:105-7.
Titulaer, M.J. et al., Treatment and Prognostic Factors for Long-Term Outcome in Patients with Anti-NMDA Receptor Encephalitis: an Observational Cohort Study. Lancet Neurol. 2013; 12(2):157-65.

* cited by examiner

*Primary Examiner* — My-Chau T. Tran
(74) *Attorney, Agent, or Firm* — Ballard Spahr LLP

(57) ABSTRACT

The disclosure relates to compositions and methods for treating a subject suffering from anti-NMDA receptor encephalitis. The method comprises administering to a patient in need of treatment an effective amount of tramadol before and/or during administration of therapeutic plasma exchange.

25 Claims, No Drawings

METHODS OF TREATING ANTI-NMDA RECEPTOR ENCEPHALITIS WITH TRAMADOL

CROSS REFERENCE TO RELATED APPLICATIONS

This application claims the benefit of U.S. Provisional Application No. 62/634,248, filed on Feb. 23, 2018. The entire content of which is hereby incorporated by reference.

BACKGROUND

Anti-N-methyl-D-aspartate receptor (anti-NMDAR) encephalitis is a form of inflammation of the brain that can be lethal. It has a high probability of recovery with treatment, but the recovery and treatment process can take months and requires hospitalization. Relapse is common. New compositions and methods are needed to reduce the occurrence of a relapse and improve recovery time.

SUMMARY

Disclosed herein are methods of treating anti-NMDA receptor encephalitis in a subject, the methods comprising: (a) identifying a subject in need of treatment; and (b) administering to the subject a therapeutically effective amount of tramadol before or during therapeutic plasma exchange.

Disclosed herein are methods of increasing the efficacy of therapeutic plasma exchange in a subject, the methods comprising: (a) identifying a subject in need of treatment; and (b) administering to the subject a therapeutically effective amount of tramadol before or during therapeutic plasma exchange.

Disclosed herein are methods of increasing removal of NMDA receptor antibodies, the methods comprising: administering to a subject in need thereof, a therapeutically effective amount of tramadol before or during therapeutic plasma exchange.

Other features and advantages of the present compositions and methods are illustrated in the description below, and the claims.

DETAILED DESCRIPTION

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, the subject is a human. The term does not denote a particular age or sex. Thus, adult, child, adolescent and newborn subjects, as well as fetuses, whether male or female, are intended to be covered.

As used herein, the term "patient" refers to a subject afflicted with a disease, disorder or condition. The term "patient" includes human and veterinary subjects. In some aspects of the disclosed methods, the "patient" has been diagnosed with a need for treatment for treating anti-NMDA receptor encephalitis, such as, for example, prior to the administering step.

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. In an aspect, the subject may exhibit a prodrome. For example, the disease, disorder, and/or condition can be an early sign or symptom (or set of signs and symptoms) indicating the onset of a disease, disorder and/or condition before diagnostically specific signs or symptoms develop. In an aspect, the disease, disorder, and/or condition can be anti-N-methyl-D-aspartate receptor encephalitis.

Anti-N-methyl-D-aspartate receptor (anti-NMDAR) encephalitis is a rare medical condition that was first described in 2005 in females with ovarian teratomas (J. Dalmau, et al., Ann. Neurol. 61 (2007) 25-36). The disorder is characterized by one or more of the following altered mental status, psychiatric disorders, and seizures with progression to dyskinesias (J. Dalmau, et al., Ann. Neurol. 61 (2007) 25-36). The mainstay of treatment for anti-NMDAR encephalitis is immunotherapy with steroids, intravenous immunoglobulin (IVIG) and/or therapeutic plasma exchange (PLEX). These first-line therapies, however, only improve symptoms in about half of anti-NMDAR encephalitis patients within 4 weeks. As many as 57% of patients in one study required second-line therapy, including rituximab or cyclophosphamide, or both therapies. These second-line immunotherapies significantly improved the outcome in patients and led to less relapses.

In many instances, anti-NMDAR encephalitis includes a prodrome which includes headaches, hyperthermia, and in some instances nausea, vomiting, and diarrhea (J. Dalmau, et al., Ann. Neurol. 61 (2007) 25-36). The most common presenting symptom is usually altered short term memory and many patients present first to psychiatrists due to acute psychosis and agitation (J. Dalmau, et al., Ann. Neurol. 61 (2007) 25-36). Finally, the disease can progress to causing any type of seizures, a comatose state, various movement disorders, or autonomic instability (J. Dalmau, et al., Ann. Neurol. 61 (2007) 25-36; and A. Seifi and D. L. Kitchen, Management of dyskinesia in anti-NMDAR encephalitis with tramadol, Clin. Neurol. Neurosurg. 147 (2016) 105-107).

The current mainstay of treatment for this disorder is immunotherapy with steroids, intravenous immunoglobulin (WIG) and/or therapeutic plasma exchange (PLEX) (J. Dalmau, et al., Ann. Neurol. 61 (2007) 25-36). However, these first-line therapies only improve symptoms in about half of anti-NMDAR encephalitis patients within 4 weeks. As many as 57% of patients in one study went on to require second line therapy including either rituximab, cyclophosphamide or both therapies (J. Dalmau, et al., Ann. Neurol. 61 (2007) 25-36). These second line immunotherapies significantly improved outcomes in patients and led to less relapses (M. J. Titulaer, et al., Lancet Neurol. 12 (2) (2013) 157-165).

Disclosed herein are method of treating anti-NMDAR encephalitis, increasing the efficacy of PLEX and increasing the removal of NMDAR antibodies via administration of tramadol before initiating PLEX and/or during one or more sessions of PLEX. In an aspect, the administration of tramadol as described herein may facilitate the effect of PLEX, resulting in a shorter duration of the illness.

Described herein are methods comprising administering to a subject in need thereof an effective dose of tramadol. Also described herein are methods of administering tramadol to subjects in need thereof to improve one or more symptoms of anti-NMDA receptor encephalitis including but not limited to dyskinesic movements. In some aspects, the disclosed methods of administering tramadol to subjects in need thereof also can facilitate the effects of PLEX, thus reducing the duration of the illness. Currently, tramadol is approved to treat moderate to severe pain.

The methods described herein have fully cured patients with anti-NMDA receptor encephalitis. The affinity of tramadol to the NMDAR may force the detachment of the NMDAR antibody from the receptor long enough to allow PLEX to work in removing the NMDAR antibodies. As described herein, the patients' redevelopment of facial dyskinesia as tramadol wore off further supports this theory that tramadol has a higher affinity for the NMDAR.

Compositions

As disclosed herein, tramadol can be useful for treating anti-NMDAR encephalitis. Currently, there are no established treatments for removing NMDAR antibodies. Tramadol ([2-(dimethylaminomethyl)-1-(3-methoxyphenyl)cyclohexanol]; also known as Ultram™, Zytram™) is a classified as an opioid pain medication and is a µ-opioid receptor agonist and a serotonin-norepinephrine reuptake inhibitor, among others. Tramadol is known to act on the opioid receptors through its active metabolite desmetramadol. Tramadol can exist in at least four different configuration forms: (1R,2R)-isomer, (1S,2S)-isomer, (1R,2S)-isomer, and (1S,2R)-isomer. Currently, tramadol is available in tablet form or intravenous form. In an aspect, tramadol, its active metabolite and any of its isomers can be used in the methods disclosed herein.

Tramadol can be useful in the treatment of anti-NMDAR encephalitis and the removal of NMDAR antibodies in a subject. In an aspect, tramadol can be administered in a therapeutically effective amount in combination with therapeutic plasma exchange. In an aspect, tramadol can be administered in a therapeutically effective amount to facilitate the therapeutic benefit of therapeutic plasma exchange, i.e., the removal of NMDAR antibodies.

Any method known to one of ordinary skill in the art can be used to determine if a particular response is induced. Clinical methods that can assess the degree of a particular disease state can be used to determine if a response is induced. For example, in a patient with anti-NMDAR encephalitis, clinical methods can include physical examination to assess presence and/or severity of one or more symptoms of anti-MNDAR encephalitis. In an aspect, the one or symptoms of anti-NMDAR encephalitis can include dyskinesias and reduced consciousness. In an aspect, a patient can be assessed to determine after the treatments disclosed herein whether one or more symptoms of anti- NMDAR encephalitis has improved or is present. For instance, a patient can be assessed to determine whether the degree of severity of dyskinesias has decreased and/or whether the level of consciousness has improved. These assessments can be performed before and/or after each administration of tramadol in combination with one or more sessions of PLEX. Eye opening and the ability to understand or track verbal and/or nonverbal commands can be performed in patients that were, for example, comatose before or after any of the treatments disclosed herein. The particular methods used to evaluate a response will depend upon the nature of the patient's disorder, the patient's age, and sex, other drugs being administered, and the judgment of the attending clinician.

In some aspects, the methods to determine if a particular response is induced can include comparing a patient's sample with standard reference levels for a particular marker or assay. Standard reference levels can typically represent the levels derived from a large population of individuals. The reference population may include individuals of similar age, body size; ethnic background or general health as the subject in question. Thus, for example, marker levels in a patient's sample can be compared to values derived from: subjects who have not received tramadol and/or tramadol and therapeutic plasma exchange; subjects who have successfully received tramadol and/or tramadol and therapeutic plasma exchange, i.e., subjects who have successfully recovered from anti-NMDAR encephalitis; and/or subjects who are suffering from anti-NMDAR encephalitis. Any population size can be used to determine the reference levels. For example, a population of between 1 and 250, e.g., 1, 2, 3, 4, 5, 10, 15, 20, 25, 30, 40, 50, 100, 150, 200, 250 or more subjects can be used to determine the average reference levels, with greater accuracy in the measurement coming from larger sample populations.

Tramadol and/or tramadol and therapeutic plasma exchange as described herein can be administered in conjunction with other therapeutic modalities to a subject in need of therapy. Tramadol and/or tramadol and therapeutic plasma exchange can be administered prior to, simultaneously with or after treatment with other agents or regimes. For example, tramadol and/or tramadol and therapeutic plasma exchange can be administered in conjunction with standard therapies used in the treatment of anti-NMDAR encephalitis or used in the treatment of any one of the signs, symptoms or complications associated with anti-NMDAR encephalitis. In an aspect, NMDA receptors antagonists can be administered in combination with tramadol and/or tramadol and therapeutic plasma exchange as described herein. Examples of other medications/NMDA receptors antagonists include but are not limited to ketamine and or dextromethorphan or a combination thereof. Any of the NMDA receptors antagonists can be administered alone, in combination with another NMDA receptor antagonists or in combination with tramadol.

Duration of the treatment with tramadol and/or tramadol and therapeutic plasma exchange as disclosed herein can be any length of time as short as 1 s, 10 s, 15 s, 30 s, 40 s, 50 s, or 60 s to as long as 1 month, 2 months, 3 months, 5 months or 6 months. In an aspect, the treatment with tramadol and/or tramadol and therapeutic plasma exchange as disclosed herein can be 1 minute, 5 minutes, 10 minutes, 15 minutes, 30 minutes, 1 hour, 2 hours, 3 hours, 4 hours, 5 hours, 10 hours, 15 hours, 20 hours, 21 hours, 22 hours, 23 hours, 24 hours, 2 days, 3 days, 4 days, 5 days, 10 days, 15 days, 20 days, 30 days, 2 months, 3 months, 4 months, 5 months, 6 months or any time in between or longer. For example, tramadol can be administered 1 second, 2 seconds, 3 seconds, 4 seconds, 5 seconds, 10 seconds, 15 seconds, 30 seconds, 1 minute, 5 minutes, 10 minutes, 15 minutes, 30 minutes, 1 hour, 2 hours, 3 hours, 4 hours, 5 hours, 10 hours, 15 hours, 20 hours, 21 hours, 22 hours, 23 hours, 24 hours or any time (seconds, minutes, hours) in between before the administration of therapeutic plasma exchange. The frequency of the treatment can vary. In an aspect, the initial administration of tramadol can precede the initial administration of therapeutic plasma exchange by 1 second, 2 seconds, 3 seconds, 4 seconds, 5 seconds, 10 seconds, 15 seconds, 30 seconds, 1 minute, 5 minutes, 10 minutes, 15 minutes, 30 minutes, 1 hour, 2 hours, 3 hours, 4 hours, 5 hours, 10 hours, 15 hours, 20 hours, 21 hours, 22 hours, 23 hours, 24 hours or any time (seconds, minutes, hours) in between or longer. In an aspect, the subsequent administration(s) of tramadol can be for part of or for the whole duration of the days that the subject receives therapeutic plasma exchange. In an aspect, the duration of the administration of the tramadol and therapeutic plasma exchange can be between 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days or longer. Once treatment with tramadol begins, tramadol can be administered to the subject in need thereof every 8 hours for the duration of the therapeutic plasma exchange. The duration of the therapeutic plasma exchange can be one or more sessions of therapeutic plasma exchange.

The particular dosage of a pharmaceutical composition to be administered to the subject will depend on a variety of considerations including the nature of the disease, disorder or condition (e.g., the severity of the anti-NMDAR encephalitis), the schedule of administration, the age and physical characteristics of the subject and other considerations known to one of ordinary skill in the art.

In an aspect, the treatment regimen can be 100 mg of tramadol three times a day starting from the time of suspicion of anti-NMDAR encephalitis or from the time of anti-NMDAR encephalitis laboratory diagnosis. In aspect, said treatment regimen can be continued for as long as needed until one or more symptoms improve and/or resolve. In an aspect, said treatment regimen can be carried out for one or more days, one or more weeks, or one or more months until the one or symptoms improve or resolve. In an aspect, tramadol can be administered before the initial start of therapeutic plasma exchange. In an aspect, tramadol can be administered throughout the course of one or more sessions of therapeutic plasma exchange. In an aspect, tramadol administration can overlap with any of the individual sessions of therapeutic plasma exchange. In an aspect, tramadol can be administered after therapeutic plasma exchange therapy has ended. In an aspect, 50 to 150 mg of tramadol can be administered every 4, 6, 8, 10, 12, 14, 16, 18, 20, 22, 24 hours. In an aspect, 50 to 150 mg of tramadol can be administered every 4 to 24 hours.

The time period of therapeutic effectiveness of tramadol from a single (or multiple) dose(s) administration can last from about 60 minutes to 8 hours. In an aspect, a time period of therapeutic effectiveness of tramadol can be between 60 minutes to 480 minutes. In an aspect, the time period of therapeutic effectiveness of tramadol can be at least 60 minutes, 1 hour, 2 hours, 3 hours, 4 hours, 5 hours, 6 hours, 7 hours, or 8 hours or any time period in between.

In some aspects, tramadol can be administered in combination with other therapeutic drugs used to treat subjects suffering from anti-NMDAR encephalitis. For example, in some aspects, tramadol can be administered with PLEX (or in combination with PLEX) and one or more NMDA receptor antagonists. In an aspect, the NMDA receptor antagonists can be ketamine (iv) or dextromethorphan (enteral) or a combination thereof.

Methods of Treatment

Disclosed herein, are methods of treating anti-NMDA receptor encephalitis in a subject. The method can comprise: (a) identifying a subject in need of treatment; and (b) administering to the subject a therapeutically effective amount of tramadol before or during therapeutic plasma exchange.

Disclosed herein, are methods of increasing the efficacy of therapeutic plasma exchange in a subject. In an aspect, the methods comprise: (a) identifying a subject in need of treatment; and (b) administering to the subject a therapeutically effective amount of tramadol before or during therapeutic plasma exchange.

Disclosed herein, are methods of increasing removal of NMDA receptor antibodies. The methods can comprise administering to a subject in need thereof, a therapeutically effective amount of tramadol before or during therapeutic plasma exchange.

In an aspect, the subject can be a human. In an aspect, the subject has been diagnosed with anti-NMDAR encephalitis prior to the administering step.

In an aspect, tramadol can be administered to the subject before the administration of the therapeutic plasma exchange. In an aspect, the phrase "before therapeutic plasma exchange" can mean before the initial start of therapeutic plasma exchange or before one or more of the therapeutic plasma exchange sessions. "Before" can also mean immediately before, or seconds, minutes, hours or days before the initial start of therapeutic plasma exchange or any of the one or more therapeutic plasma exchange sessions. In an aspect, tramadol can be administered to the subject before the initial start of therapeutic plasma exchange. In an aspect, tramadol can be administered to the subject at least one day before or prior to the administration of the therapeutic plasma exchange. In an aspect, the initial administration of tramadol can be one day before the initial administration of the therapeutic plasma exchange. In an aspect, tramadol can be administered to the subject during the administration of the therapeutic plasma exchange. In an aspect, the term "during" as used herein can mean that, for example, administration of tramadol can be at the same time, along with, simultaneously with, overlapping with or in between therapeutic plasma exchange sessions. In an aspect, tramadol can be administered to the subject before and during the administration of the therapeutic plasma exchange. In an aspect, tramadol can be administered to the subject one or more times before, during or after the administration of the therapeutic plasma exchange. In an aspect, tramadol can be administered such that it overlaps with one or more sessions of therapeutic plasma exchange. In an aspect, tramadol can be administered to a subject at least once before the initial administration of therapeutic plasma exchange and in combination with one or more sessions of therapeutic plasma exchange. For example, tramadol can be administered at least once before the initial administration of therapeutic plasma exchange, and then again either before, at the same time or in between one or more therapeutic plasma exchange administrations or sessions. In an aspect, tramadol can be administered to the subject between 10 to 20 days. In an aspect, tramadol can be administered to the subject before and during the administration of the therapeutic plasma exchange, wherein the therapeutic plasma exchange can be administered to the subject between 10 to 20 days. In an aspect, tramadol can be administered to the subject about 1 to 2 hours prior to each administration of therapeutic plasma exchange.

In an aspect, the administration of tramadol can increase the efficacy of the therapeutic plasma exchange compared to the administration of the therapeutic plasma exchange in the absence of the administration of tramadol. In an aspect, the administration of tramadol to a subject before and/or during the administration of therapeutic plasma exchange can reduce one or more symptoms of anti-NMDAR encephalitis. In an aspect, the one or more symptoms of anti-NMDA encephalitis can be observed after a single administration of tramadol to a subject before and/or during the administration of therapeutic plasma exchange. In an aspect, the administration of tramadol to a subject before and/or during the administration of therapeutic plasma exchange can reduce the number or frequency of therapeutic plasma exchange sessions.

Plasma exchange therapy can be associated with one or more side effects as well as increase, for example, a patient's risk of infection (e.g., blood infection, plasma exchange catheter infection); and hypotension (with each session or administration). In an aspect, the administration of tramadol to a subject before and/or during the administration of therapeutic plasma exchange can reduce one or more side effects associated with plasma exchange therapy, the risk of infection and hypotension.

In an aspect, the administration of tramadol to a subject before and/or during the administration of therapeutic plasma exchange can increase a subject's recovery time compared to the administration of the therapeutic plasma exchange in the absence of the administration of tramadol. In an aspect, the administration of tramadol can facilitate the removal of NMDAR antibodies via therapeutic plasma exchange compared to the administration of the therapeutic plasma exchange in the absence of the administration of tramadol. The period of infusion of therapeutic plasma exchange therapy can be 1 hour, 2 hours, 3 hours or 4 hours or any time in between. In an aspect, the administration of tramadol as described herein can reduce the number of administrations (or sessions) of therapeutic plasma exchange.

In an aspect, tramadol can be administered enterally or parentally or in a combination thereof. In an aspect, the parental administration can be intravenous, subcutaneous, intramuscular or direct injection.

In an aspect, the therapeutically effective amount of tramadol can be about 100 mg. In an aspect, the therapeutically effective amount of tramadol can be 50 to 150 mg. In an aspect, tramadol can be administered in a range of 50 to 150 mg three times a day. In an aspect, the timing of the administration of tramadol can be adjusted on the days that the patient also receives therapeutic plasma exchange therapy. In an aspect, the therapeutically effective amount of tramadol can be administered 1 to 2 hours prior to the initiation of therapeutic plasma exchange. In an aspect, the administration of the therapeutically effective amount of tramadol can be continued on days where the patient does not receive therapeutic plasma exchange therapy. In an aspect, tramadol can be administered every 8 hours. In an aspect, tramadol can be administered to the subject for the duration of time that the subject is undergoing therapeutic plasma exchange.

Therapeutic plasma exchange is a treatment that removes plasma from the blood. The removed plasma is then replaced with a substitute. Plasma is the liquid portion of the blood and carries blood cells and other substances throughout the body. In the case of anti-NMDAR encephalitis, the plasma can comprise an abnormal substance, for example, NMDAR antibodies that can trigger one or more symptoms. In an aspect, therapeutic plasma exchange can remove NMDAR antibodies from the plasma. In an aspect, therapeutic plasma exchange can relieve one or more symptoms of anti-NM-DAR encephalitis. Generally, two or more therapeutic plasma exchange treatments can be performed. In an aspect, one or more therapeutic plasma exchange treatments (or sessions) can be administered. Each administration of therapeutic plasma exchange can take between 2 and 4 hours. In an aspect, a subject diagnosed with anti-NMDAR encephalitis can receive between 5 to 10 therapeutic plasma exchange administrations or sessions. In an aspect, administration of therapeutic plasma exchange can occur one or more times a week. In an aspect, administration of therapeutic plasma exchange can occur approximately 3 times a week. For example, if a subject has a confirmed anti-NMDAR encephalitis diagnosis by positive CSF or serum test, then a large vascular catheter can be inserted in a neck vein of the subject, often referred to as plasma exchange access. The vascular access to the therapeutic plasma exchange or PLEX machine is similar to a kidney hemodialysis machine. The PLEX machine can drain the blood from this vascular access and filter the blood and return it through the same vascular access. This filter blindly removes both "good" and "bad" antibodies from the blood. The process of therapeutic plasma exchange therapy generally takes about 2-4 hours. The administration of therapeutic plasma exchange can cause, for example, hypotension. In such instances, the administration of therapeutic plasma exchange can be aborted around 2 hours after the start. If the subject maintains a healthy or adequate blood pressure, the administration of therapeutic plasma exchange can continue for about 4 hours. The subject can then rest the next day. In an aspect, therapeutic plasma exchange therapy can then be administered a second time, for example, the day after the day of rest (e.g., day 3). In an aspect, therapeutic plasma exchange therapy can be administered every other day for a total of about 5 to 10 times (e.g., about 10-20 days). In an aspect, the methods described herein can be repeated for as long as needed. In aspect, the administration to a subject a therapeutically effective amount of tramadol before or during therapeutic plasma exchange can be performed 1-5 times, 6-10 times, 11-15 times, or 16-20 times. In aspect, said administration can be performed less than 15 times. In an aspect, the administration to a subject a therapeutically effective amount of tramadol before or during therapeutic plasma exchange can improve one or more symptoms associated with anti-NMDAR encephalitis after 1-3 treatments, after 4-5 treatments, 6-10 treatments or 11-15 treatments.

In an aspect, a therapeutically effective amount of a pharmaceutical composition comprising tramadol and a pharmaceutically acceptable carrier can be administered to the subject. In an aspect, the administration of tramadol and therapeutic plasma exchange can reduce one or more symptoms of anti-NMDAR encephalitis. In an aspect, one or more of the symptoms of anti-NMDAR encephalitis can be reduced over a period of at least 60 minutes to about 180 minutes. In an aspect, one or more of the symptoms of anti-NMDAR encephalitis can be reduced over a period of at least 1 day, at least 2 days, at least 3 days, at least 4 days, at least 5 days, at least 10 days or more. Anti-NMDA receptor encephalitis is an autoimmune disorder that targets the NMDA receptor. It is a form of brain inflammation. It can be associated with tumors, such as teratomas of the ovaries. In an aspect, the one or more symptoms of anti-NMDAR encephalitis can include but are not limited to behavioral changes (e.g., agitation, paranoia, psychosis and violent behaviors); seizures and bizarre movements of the lips and mouth and pedaling motions with legs or hands; impaired cognition; memory deficits; and speech problems (including aphasia); psychiatric (e.g., delusions, perceptual disturbances and disorganized thoughts); autonomic dysfunction; hypoventilation, cerebellar ataxia, hemiparesis, loss of consciousness or catatonia. In an aspect, one or more symptoms of anti-NMDAR encephalitis can be reduced immediately or after a few minutes, hours or days after each administration of tramadol before and/or during administration of therapeutic plasma exchange. For example, the reduced symptoms or clinical improvement can be opening of the subject's eyes and/or stopping or reduced severity of dyskinesias (e.g., the non-voluntary frequent facial and extremity movements).

The pharmaceutical compositions described herein can be formulated to include a therapeutically effective amount of a tramadol. In an aspect, tramadol can be contained within a pharmaceutical formulation. In an aspect, the pharmaceutical formulation can be a unit dosage formulation.

Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to anti-NMDAR encephalitis.

The pharmaceutical compositions in combination with therapeutic plasma exchange therapy described herein can be administered to the subject (e.g., a human patient) in an amount sufficient to delay, reduce, prevent or reverse the onset or duration of anti-NMDAR encephalitis in a subject. Accordingly, in some aspects, the patient can be a human patient. In therapeutic applications, compositions and therapeutic plasma exchange therapy can be administered to a subject (e.g., a human patient) already expressing or diagnosed with one or more anti-NMDAR encephalitis symptoms in an amount sufficient to at least partially improve a sign or symptom or to inhibit the progression of (and preferably arrest) the symptoms of the condition, its complications, and consequences. An amount adequate to accomplish this is defined as a therapeutically effective amount. A therapeutically effective amount of a pharmaceutical composition can be an amount that achieves a cure or reverses one or more symptoms of anti-NMDAR encephalitis, but that outcome is only one among several that can be achieved. As noted, a therapeutically effect amount includes amounts that provide a treatment in which the onset, progression or expression of one or more of the signs or symptoms associated with anti-NMDAR encephalitis is delayed, hindered, or prevented, or the one or more symptoms associated with anti-NMDAR encephalitis is reduced, ameliorated or reversed. One or more of the signs or symptoms can be less severe. Recovery can be accelerated in an individual who has been treated.

Amounts effective for this use can depend on the severity of the symptoms of anti-NMDAR encephalitis and the weight and general state and health of the subject, but generally range from about 0.25 mg to about 150 mg of an equivalent amount of the tramadol per dose per subject.

The total effective amount of a tramadol as disclosed herein can be administered to a subject as a single dose, either as a bolus or by infusion over a relatively short period of time, or can be administered using a fractionated treatment protocol in which multiple doses are administered over a more prolonged period of time. Alternatively, continuous intravenous infusions sufficient to maintain therapeutically effective concentrations in the blood are also within the scope of the present disclosure.

The therapeutically effective amount or dosage of the tramadol used in the methods as disclosed herein applied to mammals (e.g., humans) can be determined by one of ordinary skill in the art with consideration of individual differences in age, weight, sex, other drugs administered and the judgment of the attending clinician. Variations in the needed dosage may be expected. Variations in dosage levels can be adjusted using standard empirical routes for optimization. The particular dosage of a pharmaceutical composition to be administered to the patient will depend on a variety of considerations (e.g., the severity of signs or symptoms of the anti-NMDAR encephalitis), the age and physical characteristics of the subject and other considerations known to those of ordinary skill in the art. In an aspect, the dosage of tramadol can be 25, 50, 100, 200, 300 or 400 mg total. In an aspect, tramadol can be administered intravenously. In an aspect, tramadol can be administered enterally. The symptoms of anti-NMDAR encephalitis can be reversed via administration of tramadol before the initial administration of therapeutic plasma exchange; or via administration of tramadol during the administration of therapeutic plasma; or a combination thereof.

Pharmaceutical Compositions

As disclosed herein, are pharmaceutical compositions, comprising tramadol and a pharmaceutical acceptable carrier described herein. In some aspects, tramadol can be formulated for intravenous administration. In some aspects, tramadol can be formulated for enteral administration. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The compositions can be administered directly to a subject. Generally, the compositions can be suspended in a pharmaceutically acceptable carrier (e.g., physiological saline or a buffered saline solution) to facilitate their delivery. Encapsulation of the compositions in a suitable delivery vehicle (e.g., polymeric microparticles or implantable devices) may increase the efficiency of delivery.

The compositions can be formulated in various ways for parenteral or nonparenteral administration. Methods of enteral administration can involve the esophagus, stomach and small and large intestines. Methods of enteral administration can also include oral, sublingual and rectal.

Where suitable, oral formulations can take the form of tablets, pills, capsules, or powders, which may be enterically coated or otherwise protected. Sustained release formulations, suspensions, elixirs, aerosols, and the like can also be used.

Pharmaceutically acceptable carriers and excipients can be incorporated (e.g., water, saline, aqueous dextrose, and glycols, oils (including those of petroleum, animal, vegetable or synthetic origin), starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, ethanol, and the like). The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in "Remington's Pharmaceutical Sciences" by E.W. Martin, which is herein incorporated by reference. Such compositions will, in any event, contain an effective amount of the compositions together with a suitable amount of carrier so as to prepare the proper dosage form for proper administration to the patient.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used. Thus, compositions can be prepared for parenteral administration that includes tramadol dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules.

Articles of Manufacture

The composition described herein can be packaged in a suitable container labeled, for example, for use as a therapy to treat anti-NMDAR encephalitis. Accordingly, packaged products (e.g., sterile containers containing the composition described herein and packaged for storage, shipment, or sale at concentrated or ready-to-use concentrations) and kits, including at least tramadol as described herein and instructions for use, are also within the scope of the disclosure. A product can include a container (e.g., a vial, jar, bottle, bag, or the like) containing the composition described herein. In addition, an article of manufacture further may include, for example, packaging materials, instructions for use, syringes, buffers or other control reagents for treating or monitoring the condition for which prophylaxis or treatment is required. The product may also include a legend (e.g., a printed label or insert or other medium describing the product's use (e.g., an audio- or videotape)). The legend can be associated with the container (e.g., affixed to the container) and can describe the manner in which the compound therein should be administered (e.g., the frequency and route of administration), indications therefor, and other uses. The composition can be ready for administration (e.g., present in doseappropriate units), and may include a pharmaceutically acceptable adjuvant, carrier or other diluent. Alternatively, the compounds can be provided in a concentrated form with a diluent and instructions for dilution.

In an aspect, tramadol can be co-formulated with a therapeutic plasma exchange kit. In an aspect, tramadol and a therapeutic plasma exchange kit can be co-packaged.

EXAMPLES

Example 1: Tramadol Increases the Efficacy of Therapeutic Plasma Exchange in Anti-NMDAR Encephalitis Described herein is a previously healthy 31 year old female with newly diagnosed seizures and schizophrenia. The patient's symptoms began with an episode of "psychosis" for which she was diagnosed with schizophrenia. She progressed to having generalized tonic-clonic seizures, and was was monitored for continuous electroencephalographic (EEG) one month after the start of her symptoms. Her EEG showed status epilepticus thereby requiring her intubation and initiation of two more anti-epileptics. At that time, she was started on solumedrol 1 g each day for five days along with the last two days of the steroid course being completed. She failed to improve any of her symptoms. Her anti-epileptic medications were escalated to include levetiracetam, phenobarbital, and lacosimide. Her EEG pattern showed continuous generalized polymorphic delta activity at 2-3 Hz without evidence of epileptiform discharges or seizures. She continued to have oral dyskinesias that mainly consisted of lip smacking and biting motion with her jaw.

Her tongue had continuous movement roving throughout her mouth, and her eyes continued to open and close constantly. She underwent a lumbar puncture, which was positive for anti-NMDAR Immunoglobulin G at a ratio of 1:120 (IgG) (Euroimmun commercial Biochip cell-based assay) analyzed by ARUP Laboratories (Salt Lake City, Utah). The assay used a semi-quantitative indirect immunofluorescence on human embryonic kidney cell cultures expressing recombinant NMDA receptors (transfected HEK 293 cells). The initial protein on the CSF sample was 49 mg/dl with a glucose of 43 mg/dl. There were 179 white blood cells present with a 97% lymphocytic predominance and 2 RBCs. Finally, oligoclonal bands were positive at 8, with negative results for AMPA, GAD, GABA-R antibodies. NMDA receptor antibodies were not sent from her serum. Patient had negative CT scans for occult malignancies. The day after a confirmed positive result for anti-NMDAR antibody, she was subsequently started on a course of PLEX every other day, in fact the PLEX was started 44 days after her first presentation of anti-NMDAR encephalitis symptoms. She underwent three of the five PLEX sessions before it was withheld due to toxic megacolon from *Clostridium difficile* colitis that required a total colectomy. Throughout her three PLEX sessions, she was obtunded and not following commands with only minimal improvement in her facial dyskinesias with ketamine at 20 mcg/kg/min. Six days after her colectomy, PLEX was restarted for another five sessions. She was pre-treated with tramadol 100 mg enterally three times a day, specifically one hour before each subsequent five PLEX sessions. In contrast to the earlier PLEX sessions, the patient rapidly responded to both PLEX and tramadol. Her facial dyskinesias resolved after the first PLEX session and she opened her eyes spontaneously immediately following the first PLEX session. By the end of her third PLEX session in combination with the tramadol, she began to follow commands. By the end of her fifth PLEX session, she was alert and awake enough to interact with her care providers and her facial dyskinesias had completely resolved. She was downgraded from the intensive care unit one week after the last PLEX, at the hospital day 36 (97 days after first symptoms) alert, awake, and following complex commands. At her follow up appointment, nine months after symptoms onset, she continues to do well and is back to work, has not had any recurrent symptoms, and no lasting neurologic effects.

Tramadol is a weak centrally acting µ-opioid receptor agonist, but additionally acts to inhibit NMDARs at clinically relevant levels (K. Hara, et al., Anesth. Analg. 100 (2005) 1400-1405). The oral formulation of tramadol has a peak onset of approximately 60 min and is completely absorbed with a higher brain concentration than in plasma (S. Grond and A. Sablotzki, Clin. Pharmacokinet. 43 (2004) 879-923). The increased availability in the brain tissue along with its fast peak onset of action makes it an appealing choice for treatment. The most commonly reported side effects of tramadol include: dizziness, tiredness, drowsiness, fatigue, nausea, vomiting, sweating and dry mouth (S. Grond and A. Sablotzki, Clin. Pharmacokinet. 43 (2004) 879-923). In less than 1% of patients, serious side effects of hypotension, circulatory collapse, pruritus, sleep disorders, somnolence, abdominal pain, and tachycardia occur (S. Grond and A. Sablotzki, Clin. Pharmacokinet. 43 (2004) 879-923). Studies have shown that PLEX for anti-NMDAR encephalitis is effective, but lacks rapid correction of symptoms (K. Hara, et al., Anesth. Analg. 100 (2005) 1400-1405). The large volume of distribution of NMDAR antibodies and long half-life makes PLEX sessions a desirable first-line therapy, but as shown in a large multi-institutional observational study this treatment protocol is limited as just 53% of patients who receive first-line immunotherapy or tumor removal experience improvement in symptoms within 4 weeks (J. Dalmau, et al., Ann. Neurol. 61 (2007) 25-36; and M. J. Titulaer, et al., Lancet Neurol. 12 (2) (2013) 157-165). In anti-NMDAR encephalitis patients treated with first-line immunotherapy, nearly 75% experienced resolved symptoms by 4 months (J. Dalmau, et al., Ann. Neurol. 61 (2007) 25-36; and M. J. Titulaer, et al., Lancet Neurol. 12 (2) (2013) 157-165). In patients requiring second-line immunotherapy, roughly half of patients recovered by 8 months (J. Dalmau, et al., Ann. Neurol. 61 (2007) 25-36; and M. J. Titulaer, et al., Lancet Neurol. 12 (2) (2013) 157-165). Additionally, new studies are showing that the earlier and more aggressive treatment leads to better outcomes (M. J. Titulaer, et al., Lancet Neurol. 12 (2) (2013) 157-165; and M. Nosadini, et al., Expert Rev. Neurother. 15 (12) (2015) 1391-1419). Based on the case study described herein, PLEX therapy on its own is probably insufficient for quick treatment as it cannot clear the strongly bound NDMAR antibodies from the NMDARs, which is needed for the resolution of symptoms.

On the other hand, when PLEX is administered with a pre-treatment of tramadol, PLEX successfully controlled the dyskinesia and allowed the patient to become alert and oriented as described herein. Tramadol non-competitively inhibits NMDARs in a concentration dependent manner (A. Seifi and D. L. Kitchen, Clin. Neurol. Neurosurg. 147 (2016) 105-107; and K. Hara, et al., Anesth. Analg. 100 (2005) 1400-1405). Therefore, this study suggests that PLEX administered with a pre-treatment of tramadol more likely works quickly and improves dyskinesias, for example, because tramadol has a higher affinity for the NMDAR. The affinity of tramadol to the NMDAR forces the detachment of the NMDAR antibody from the receptor long enough to allow PLEX to work in removing the NMDAR antibodies. No studies have been published that directly compare the binding affinity between tramadol and the NMDA antibody. The patients' redevelopment of facial dyskinesia as tramadol wore off further supports this theory that tramadol has a higher affinity for the NMDAR (A. Seifi, and D. L. Kitchen, Clin. Neurol. Neurosurg. 147 (2016) 105-107). Additionally, the resolved symptoms after a full cycle of PLEX therapy with tramadol administration also support this theory as multiple sessions are needed to fully clear the NMDAR antibodies. This study described herein shows that tramadol is a safe and an effective treatment for anti-NMDAR encephalitis. Further, tramadol can lead to a faster effect of PLEX and a shorter duration of symptoms in patients with anti-NMDAR encephalitis.

In patients with anti-NMDAR encephalitis, PLEX therapy is a mainstay for treatment, but is slow in effectively treating a majority of patients with anti-NMDAR encephalitis. In this case study of a patient with anti-NMDAR encephalitis, PLEX therapy alone was insufficient in quickly treating the debilitating symptoms. However, when PLEX therapy was administered after pre-treating with tramadol, the patient achieved a rapid and observable recovery. Although the exact mechanism of tramadol when administered with PLEX therapy in anti-NMDAR encephalitis is not fully understood, the potential for a shorter duration of the illness is evident with this treatment, which has the potential for many therapeutic and financial benefits.

What is claimed is:

1. A method of treating anti-NMDA receptor encephalitis in a subject, the method comprising:
    (a) identifying a subject in need of treatment; and
    (b) administering to the subject a therapeutically effective amount of tramadol before or during therapeutic plasma exchange.

2. The method of claim 1, wherein the subject is a human.

3. The method of claim 1, wherein tramadol is administered to the subject before the administration of the therapeutic plasma exchange.

4. The method of claim 1, wherein tramadol is administered enterally or parentally.

5. The method of claim 4, wherein the parental administration is intravenous, subcutaneous, intramuscular or direct injection.

6. The method of claim 1, wherein the therapeutically effective amount of tramadol is 50-150 mg of tramadol.

7. The method of claim 1, wherein administration of tramadol increases the efficacy of the therapeutic plasma exchange compared to the administration of the therapeutic plasma exchange in the absence of the administration of tramadol.

8. The method of claim 1, wherein tramadol is administered to the subject at least one day prior to the administration of the therapeutic plasma exchange.

9. The method of claim 1, wherein tramadol is administered to the subject for the duration of the administration of the therapeutic plasma exchange.

10. The method of claim 9, wherein tramadol and therapeutic plasma exchange are administered to the subject for about ten to twenty days.

11. A method of increasing the efficacy of therapeutic plasma exchange in a subject, the method comprising:
    (a) identifying a subject in need of treatment; and
    (b) administering to the subject a therapeutically effective amount of tramadol before or during therapeutic plasma exchange.

12. The method of claim 11, wherein the subject has been diagnosed with anti-NMDA receptor encephalitis prior to the administering step.

13. The method of claim 11, wherein the subject is a human.

14. The method of claim 11, wherein the tramadol is administered before the therapeutic plasma exchange.

15. The method of claim 14, further comprising administering the tramadol for the duration of the administration of the therapeutic plasma exchange.

16. The method of claim 11, wherein tramadol is administered enterally or parentally.

17. The method of claim 16, wherein the parental administration is intravenous, subcutaneous, intramuscular or direct injection.

18. The method of claim 11, wherein the therapeutically effective amount of tramadol is 100 mg.

19. A method of increasing removal of NMDA receptor antibodies, the method comprising: administering to a subject in need thereof, a therapeutically effective amount of tramadol before or during therapeutic plasma exchange.

20. The method of claim 19, wherein the subject is a human.

21. The method of claim 19, wherein the tramadol is administered before the administration of the therapeutic plasma exchange.

22. The method of claim 19, wherein tramadol is administered enterally or parentally.

23. The method of claim 22, wherein the parental administration is intravenous, subcutaneous, intramuscular or direct injection.

24. The method of claim 19, wherein the therapeutically effective amount of tramadol is 100 mg.

25. The method of claim 19, wherein administration of tramadol increases the efficacy of the therapeutic plasma exchange compared to the administration of the therapeutic plasma exchange in the absence of tramadol.

* * * * *